United States Patent [19]

Okabe et al.

[11] Patent Number: 4,933,458

[45] Date of Patent: Jun. 12, 1990

[54] CERTAIN GASTRIC ACID SECRETION INHIBITING SULFOXIDES

[75] Inventors: Susumu Okabe, Kyoto; Masaru Satoh, Koshigaya; Tomio Yamakawa, Kashiwa; Yutaka Nomura, Noda; Masatoshi Hayashi, Ichigaya-dai, all of Japan

[73] Assignee: Nippon Chemiphar Co., Ltd., Tokyo, Japan

[21] Appl. No.: 198,086

[22] Filed: May 24, 1988

Related U.S. Application Data

[63] Continuation-in-part of Ser. No. 2,637, Jan. 12, 1987, abandoned.

[30] Foreign Application Priority Data

Jan. 10, 1986 [JP] Japan .................................... 61-3017
Jan. 28, 1986 [JP] Japan .................................... 61-16169

[51] Int. Cl.$^5$ .......................................... C07D 471/04
[52] U.S. Cl. .................................... 546/118; 540/597; 544/350; 544/354
[58] Field of Search ................. 546/118; 514/303, 212; 540/597

[56] References Cited

U.S. PATENT DOCUMENTS 4,738,970 4/1988 Uchida et al. ...................... 546/118

Primary Examiner—Mary C. Lee
Assistant Examiner—Bernard I. Dentz
Attorney, Agent, or Firm—Sixbey, Friedman, Leedom & Ferguson

[57] ABSTRACT

Sulfoxide derivatives having the formula (I) or (V) show a gastric acid-secretion inhibitory effect:

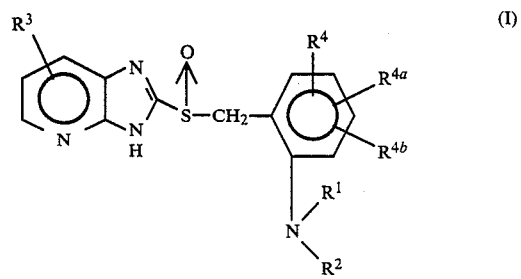

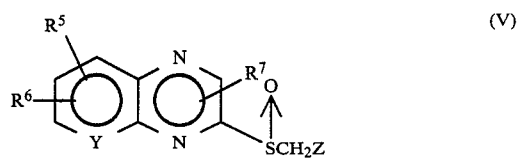

wherein each of $R^1$ and $R^2$ is hydrogen, lower alkyl, hydroxyalkyl, phenyl, phenylalkyl or cycloalkyl, $R^1$ and $R^2$ may form together with the adjacent N atom a heterocyclic group; each of $R^3$, $R^4$, $R^{4a}$, $R^{4b}$, $R^5$, $R^6$, and $R^7$ is hydrogen, halogen, lower alkoxy, lower alkyl, trifluoromethyl, or fluorine atom-containing lower alkoxy; Y is CH or N; and Z is unsubstituted or substituted 2-pyridine or 2-aminophenyl.

5 Claims, No Drawings

CERTAIN GASTRIC ACID SECRETION INHIBITING SULFOXIDES

This application is a continuation-in-part of Ser. No. 002,637, filed 01/12/87, now abandoned.

BACKGROUND OF THE INVENTION

1. Field of the Invention

This invention relates to novel sulfoxide derivatives and a pharmaceutical composition containing the same.

2. Description of Prior Art

As a gastic acid secretion inhibitor, N-cyano-N'-methyl-N''-[2-[[(5-methyl-1H-imidazol-4-yl)methyl]thio]ethyl]guanidine (available as tradename of Cimetidine) is well known.

Further, as is well known in the art to which the present invention relates, $H^{30}+K^+ATPase$ plays a principal roll in the final secretion mechanism of gastric acid in stomach cells [Scand. J. Gastroenterol., 14, 131–135 (1979)]. As a substance having $H^++K^+ATPase$ inhibitory activity, Norinium bromide is known [Proceeding of the Society for Experimental Biology and Medicine, 172, 308–315(1983)].

On the other hand, 2-[2-(3,5-dimethyl-4-methoxy)-pyridylmethylsulfinyl]-(5-methoxy)-benzimidazole [tradename: Omeprazole] has been developed as an antiucler compound having $H^++K^+ATPase$ inhibitory activity [Am. J. of Physiol., 245, G64–71 (1983)].

SUMMARY OF THE INVENTION

The present inventors have conducted extensive study and have now discovered that sulfoxide derivatives having the specific formula exhibit an excellent suppressive effect against the secretion of gastric acid owing to their specific $H^++K^+ATPase$ inhibitory effects.

Accordingly, an object of the present invention is to provide novel sulfoxide derivatives which is of value as an anti-ulcer agent.

There is provided by the invention a sulfoxide derivative having the formula (I):

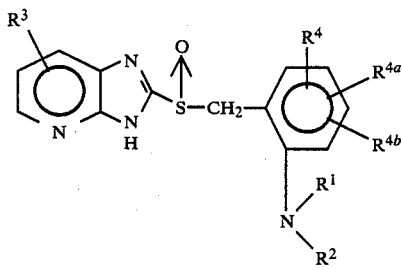

(I)

wherein each of $R^1$ and $R^2$ independently is hydrogen, an alkyl group having 1 to 6 carbon atoms (e.g., methyl, ethyl, propyl, n-butyl, isobutyl, pentyl and hexyl) which may be substituted with one or more hydroxyl, phenyl, a phenylalkyl group containing an alkyl chain of 1 to 4 carbon atoms (e.g., benzyl and phenylethyl), and a cycloalkyl group having 5 to 8 carbon atoms (e.g., cyclopentyl and cyclohexyl), $R^1$ and $R^2$ may form together with the adjacent nitrogen atom a heterocyclic group having 4 to 6 carbon atoms (e.g., piperidine), and each of $R^3$, $R^4$, $R^{4a}$ and $R^{4b}$ independently is hydrogen, halogen, hydroxyl, an alkoxy group having 1 to 6 carbon atoms (e.g., methoxy, ethoxy, propoxy and isobutoxy) which may be substituted with one or more fluorine atoms, an alkyl group having 1 to 6 carbon atoms (e.g., methyl, ethyl, propyl, n-butyl, isobutyl, pentyl and hexyl), or trifluoromethyl.

There is also provided by the invention a sulfoxide derivative having the formula (V):

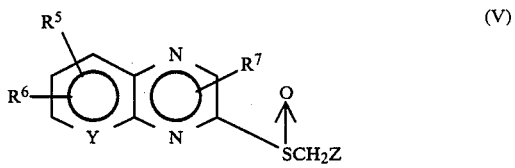

(V)

wherein each of $R^5$ and $R^6$ independently is hydrogen, halogen, an alkyl group having 1 to 6 carbon atoms (e.g., methyl, ethyl, propyl, n-butyl, isobutyl, pentyl and hexyl), or an alkoxy group having 1 to 6 carbon atoms (e.g., methoxy, ethoxy, propoxy and isobutoxy), $R^7$ is hydrogen, an alkyl group having 1 to 6 carbon atoms (e.g., methyl, ethyl, propyl, n-butyl, isobutyl, pentyl and hexyl), or an alkoxy group having 1 to 6 carbon atoms (e.g., methoxy, ethoxy, propoxy and isobutoxy), Y is CH or N, and Z is 2-pyridyl which may be substituted with one to three substituents selected from the group consisting of halogen, an alkoxy group having 1 to 6 carbon atoms (e.g., methoxy, ethoxy, propoxy and isobutoxy) which may be substituted with fluorine atom(s), an alkyl group having 1 to 6 carbon atoms (e.g., methyl, ethyl, propyl, n-butyl, isobutyl, pentyl and hexyl) or trifluoromethyl, or a 2-aminophenyl group having the formula (VI):

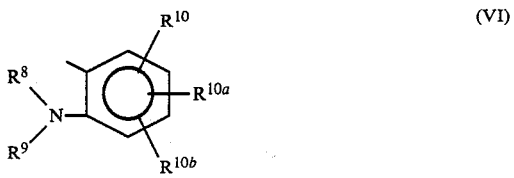

(VI)

wherein each of $R^8$ and $R^9$ independently is hydrogen, an alkyl group having 1 to 6 carbon atoms (e.g., methyl, ethyl, propyl, n-butyl, isobutyl, pentyl and hexyl) which may be substituted with one or more hydroxyl, phenyl, a phenylalkyl group containing an alkyl chain of 1 to 4 carbon atoms (e.g., benzyl and phenylethyl), and a cycloalkyl group having 5 to 8 carbon atoms (e.g., cyclopentyl and cyclohexyl), $R^8$ and $R^9$ may form together with the adjacent nitrogen atom a heterocyclic group having 4 to 6 carbon atoms (e.g., piperidine), and each of $R^{10}$, $R^{10a}$ and $R^{10b}$ independently is hydrogen, halogen, hydroxyl, an alkoxy group having 1 to 6 carbon atoms (e.g., methoxy, ethoxy, propoxy and isobutoxy) which may be substituted with one or more fluorine atoms, an alkyl group having 1 to 6 carbon atoms (e.g., methyl, ethyl, propyl, n-butyl, isobutyl, pentyl and hexyl), or trifluoromethyl.

DETAILED DESCRIPTION OF THE INVENTION

Among the sulfoxide derivatives having the formula (I), sulfoxide derivatives wherein each of $R^3$, $R^4$, $R^{4a}$ and $R^{4b}$ is hydrogen are preferred. Each of $R^1$ and $R^2$ preferably is an alkyl group having 1 to 6 carbon atoms such as methyl, ethyl, propyl or isobutyl or a cycloalkyl such as cyclopentyl or cyclohexyl.

Representative examples of the compounds of the formula (I) include:

2-(2-dimethylaminobenzylsulfinyl)imidazo[4,5-b]pyridine;
2-(2-dimethylaminobenzylsulfinyl)-7-methoxyimidazo[4,5-b]pyridine;
2-(2-dimethylaminobenzylsulfinyl)-7-methylimidazo[4,5-b]pyridine;
2-(2-diethylaminobenzylsulfinyl)imidazo[4,5-b]pyridine;
2-(2-dimethylamino-5-methylbenzylsulfinyl)imidazo[4,5-b]pyridine;
2-(2-dimethylamino-4-chlorobenzylsulfinyl)imidazo[4,5-b]pyridine;
2-(2-dimethylamino-5-methoxybenzylsulfinyl)imidazo[4,5-b]pyridine;
2-(2-dimethylamino-6-methylbenzylsulfinyl)imidazo[4,5-b]pyridine;
2-(2-dimethylamino-4-fluorobenzylsulfinyl)imidazo[4,5-b]pyridine;
2-(2-dimethylaminobenzylsulfinyl)-6-methylimidazo[4,5-b]pyridine;
2-(2-methylaminobenzylsulfinyl)imidazo[4,5-b]pyridine;
2-(2-isobutylaminobenzylsulfinyl)imidazo[4,5-b]pyridine;
2-(2-cyclopentylaminobenzylsulfinyl)imidazo[4,5-b]pyridine;
2-(2-cyclohexylaminobenzylsulfinyl)imidazo[4,5-b]pyridine;
2-[2-(N-isobutyl-N-methylamino)benzylsulfinyl]imidazo[4.5-b]pyridine;
2-[2-(N-ethyl-N-methylamino)benzylsulfinyl]imidazo[4,5-b]pyridine;
2-(2-methylamino-5-methylbenzylsulfinyl)imidazo[4,5-b]pyridine;
2-(2-isobutylamino-5-methylbenzylsulfinyl)imidazo[4,5-b]pyridine;
2-(5-methoxy-2-methylaminobenzylsulfinyl)imidazo[4,5-b]pyridine;
2-(2-cyclopentylamino-5-methylaminobenzylsulfinyl)imidazo[4,5-b]pyridine;
2-(2-aminobenzylsulfinyl)imidazo[4,5-b]pyridine;
2-(2-piperidinobenzylsulfinyl)imidazo[4,5-b]pyridine;
2-(2-methylamino-5-hydroxybenzylsulfinyl)imidazo[4,5-b]pyridine;
2-(2-dimethylamino-5-hydroxylbenzylsulfinyl)imidazo[4,5-b]pyridine; and
2-(2-hydroxyethylaminobenzylsulfinyl)imidazo[4,5-b]pyridine.

The sulfoxide derivative having the formula (I) can be advantageously prepared by a process which comprises:
reacting a mercapto derivative having the formula (II):

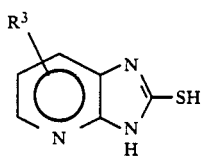

(II)

wherein $R^3$ has the same meaning as above, with a compound having the formula (III):

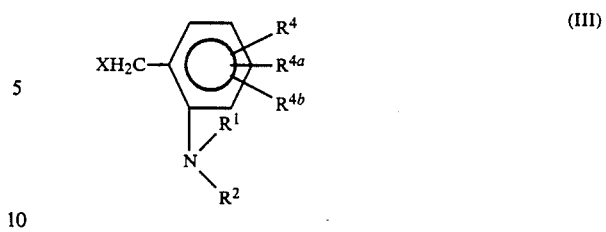

(III)

wherein each of $R^1$, $R^2$, $R^4$, $R^{4a}$ and $R^{4b}$ has the same meaning as above, and X is a reactive group, or a salt thereof to obtain a compound having the formula (IV):

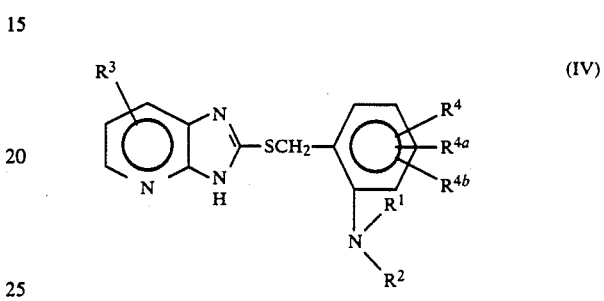

(IV)

wherein each of $R^1$, $R^2$, $R^3$, $R^4$, $R^{4a}$ and $R^{4b}$ has the same meaning as above, and
oxidizing the compound having the formula (IV).

The starting compound having the formula (II) can be prepared by bringing a diaminopyridine or its derivative into contact potassium xanthogenate in an alcoholic solvent.

The reactive group (X) of the compound having the formula (III) can be a halogen atom such as chlorine or bromine: a sulfonyloxy group such as methylsulfonyloxy or toluenesulfonyloxy; or acetoxy.

The reaction of the compound (II) and the compound (III) can be performed at a temperature from room temperature to the reflux temperature for 30 min. to 24 hrs., in an inert solvent such as benzene, ethanol or acetone. The reaction can be carried out in the presence of an alkali agent such as NaOH, KOH, $K_2CO_3$ or $NaHCO_3$, for trapping an acid produced in the reaction.

The salt of the compound (III) can be an inorganic acid salt such as hydrochloride or sulfate, or an organic acid salt such as benzoate.

The oxidation of the compound (IV) can be performed in the conventional manner. For instance, the compound (IV) can be oxidized using an oxidizing agent such as hydrogen peroxide, an inorganic peroxide (e.g., m-chloroperbenzoic acid), or sodium hypochlorite. The reaction can be performed in an inert solvent such as chloroform, dichloromethane, methanol, or ethyl acetate at a temperature ranging from $-30°$ C. to $50°$ C., preferably $-15°$ C. to $5°$ C.

Among the sulfoxide derivatives having the formula (V), sulfoxide derivatives wherein each of $R^5$, $R^6$ and $R^7$ is hydrogen are preferred. Each of $R^8$ and $R^9$ preferably is an alkyl group having 1 to 6 carbon atoms such as methyl or ethyl, cyclopentyl, or cyclohexyl.

Representative examples of the compounds of the formula (V) include:
2-(2-pyridylmethylsulfinyl)quinoxaline;
3-methyl-2-(2-pyridylmethylsulfinyl)quinoxaline;
2-[2-(4-methoxypyridyl)methylsulfinyl]-3-methylquinoxaline:

3-methyl-2-[2-(3-methylpyridyl)methylsulfinyl]quinoxaline;

6,7-dimethyl-2-(2-pyridylmethylsulfinyl)quinoxaline;

2-methyl-3-(2-pyridylmethylsulfinyl)pyrido[2,3-b]pyrazine;

2-(2-dimethylaminobenzylsulfinyl)quinoxaline;

2-(2-dimethylaminobenzylsulfinyl)-3-methylquinoxaline;

2-(2-dimethylaminobenzylsulfinyl)-3,6,7-trimethylquinoxaline;

2-(2-dimethylamino-3-methylbenzylsulfinyl)-3-methylquinoxaline;

2-(2-dimethylamino-5-methylbenzylsulfinyl)-3-methylquinoxaline;

2-(2-dimethylamino-5-methoxybenzylsulfinyl)-3-methylquinoxaline;

2-(2-diethylaminobenzylsulfinyl)quinoxaline;

7-chloro-2-(2-pyridylmethylsulfinyl)quinoxaline;

6,7-dichloro-2-(2-dimethylaminobenzylsulfinyl)quinoxaline;

2-(2-dimethylamino-4-chlorobenzylsulfinyl)-3-methyl-1-quinoxaline;

2-(2-dimethylaminobenzylsulfinyl)-6-methoxyquinoxaline; and 2-(2-dimethylaminobenzylsulfinyl)-3-methoxyquinoxaline.

The sulfoxide derivative having the formula (V) can be advantageously prepared by a process which comprises:

reacting a mercapto derivative having the formula (VII):

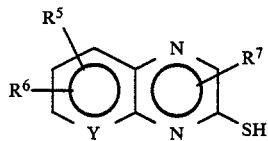

(VII)

wherein each of $R^5$, $R^6$, $R^7$ and Y has the same meaning as above, with a compound having the formula (VIII):

 QCH$_2$Z    (VIII)

wherein Z has the same meaning as above, and Q is a reactive group, or a salt thereof to obtain a compound having the formula (IX):

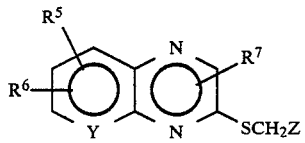

(IX)

wherein each of $R^5$, $R^6$, $R^7$, Y and Z has the same meaning as above, and oxidizing the compound having the formula (IX).

The starting compound having the formula (VII) can be prepared from a diamino compound in the conventional manner. For instance, 2-mercapto-3-methylquinoxaline can be prepared by a process described in J. Org. Chem., 21, 470 (1956).

The reactive group (Q) of the compound having the formula (VIII) can be a halogen atom such as chlorine or bromine; a sulfonyloxy group such as methylsulfonyloxy or tolunesulfonyloxy; or acetoxy.

The reaction of the compound (VII) and the compound (VIII) can be performed at a temperature from room temperature to the reflux temperature for 30 min. to 24 hrs., in an inert solvent such as benzene, ethanol or acetone. The reaction can be carried out in the presence of an alkali agent such as NaOH, KOH, K$_2$CO$_3$ or NaHCO$_3$, for trapping an acid produced in the reaction.

The salt of the compound (VIII) can be an inorganic acid salt such as hydrochloride or sulfate, or an organic acid salt such as benzoate.

The oxidation of the compound (IX) can be performed in the conventional manner. For instance, the compound (IX) can be oxidized using an oxidizing agent such as hydrogen peroxide, an organic peroxide (e.g., m-chloroperbenzoic acid), or sodium hypochlorite. The reaction can be performed in an inert solvent such as chloroform, dichloromethane, methanol, or ethyl acetate at a temperature ranging from $-30°$ C. to $-50°$ C., preferably $-15°$ C. to $5°$ C.

Acute toxicity of the sulfoxide derivatives of the formula (I) or (V) have been determined in oral administration. It has been confirmed by observation of three days after oral administration to dog that these compounds show no noticeable side-effects at a dose of 100 mg/kg.

Further, it has been confirmed that the sulfoxide derivatives of the formula (I) or (V) according to the invention are of value as a cytoprotective agent for gastrointestinal tract and can be utilized for the treatment or prevention of a non-gastric-acid-induced, non-traumatically-induced, non-neoplastic gastrointestinal inflammatory disease in a mammal suffering from or particularly susceptible to the development of said disease, as disclosed in U.S. Pat. No. 4,359,465 (Ruwart).

The anti-ulcer agent for gastrointestinal tract containing a sulfoxide derivative of the formula (I) or (V) can be administered orally or parenterally. Examples of the preparation forms for oral administration include tablets, capsules powder, granules, and syrup. In the formulation of these preparations, there can be used excipients, disintegrants, binders, lubricants, pigments, diluents and the like which are commonly employed in the art. Examples of the excipients include dextrose and lactose. Examples of the disintegrants inlcude starch and carboxymethylcellulose. Examples of the lubricants include magnesium stearate and talc. Examples of the binders include hydroxypropylcellulose, gelatin and polyvinylpyrrolidone.

The dose is generally not more than 500 mg/day, preferably about 100 μg/day to 300 mg/day, for an adult. The dose can be either increased or decreased depending upon the age and other conditions.

The present invention is further described by the following examples.

(1) H$^+$ +K$^+$ATPase inhibitory effect

Following the method of Forte et al [J. Applied Physiol., 32, 714–717 (1972)], gastric acid secretory cells of a rabbit gastric mucosa were isolated and vesicle containing H$^+$+K$^+$ATPase was prepared by centrifuging the cells in Ficoll of discontinuous density gradient. After the enzyme was incubated at room temperature for 25 min. in 0.5 ml of a solution which contained 5 mM of an imidazole buffer (ph6.0) and $2\times40^{-4}$M of each test compound, the mixture was heated to 37° C. at which it was allowed to stand for further 5 min. To the mixture was added 0.5 ml of a solution which contained 4 mM of magnesium chloride, 80 mM of an imidazole buffer (pH 7.4), 20 mM of potassium chloride and 4 mM of ATP. The resulting mixture was caused to react at 37° C. for 15 min., and 1 ml of a 24% solution of trichloroacetic acid was then added to terminate the reaction. The inorganic phosphorus liberated was quantitatively analyzed by the method proposed by Taussky and Shorr [J. Biol. Chem., 202, 675– 685 (1953)]. The $K^+$-dependent activity of the ATPase was determined by substracting its activity obtained when no potassium chloride was contained. The results are set forth in Table 1 in which Compounds Nos. 1–7 are the sulfoxide derivatives prepared in the hereinafter-described Examples 1–7, respectively.

TABLE 1

| Test Compound No. | $H^+ + K^+$ ATPase Inhibitory Effect (%) |
| --- | --- |
| 1 | 92.3 |
| 2 | 96.8 |
| 3 | 99.5 |
| 4 | 89.4 |
| 5 | 100 |
| 6 | 100 |
| 7 | 80.8 |

(2) Inhibitory action against secretion of gastric acid

Male Donryu rats having a body weight of 200 to 250 g and fasting (while allowing free access to water) for 24 hours were employed for the present test which was performed in accordance with the conventional method [Shay, H. et al., Gastroenterology, 5, 43–61 (1945)].

Under ether anesthesia, the pylorus of the rat was ligated and each test compound was administered intraduodenally. Four hours later, each rat was killed and the stomach was removed to collect the gastric juice. The inhibitory action was determined by comparing the acid output which was obtained by titration to ph 7.0 with 0.1-N NaOH by means of an automatic titrator, with the corresponding value of a control rate prepared in the same manner except that a vehicle alone was administered. The results are set forth in Table 2.

TABLE 2

| Test Compound No. | Dose (mg/kg) | Suppresive action against secretion of gastric acid (%) |
| --- | --- | --- |
| 1 | 100 | 95.1 |
|  | 30 | 79.0 |
|  | 10 | 53.0 |
| 2 | 100 | 54.8 |
| 3 | 100 | 54.7 |
| 4 | 100 | 96.7 |
| 5 | 100 | 55.1 |
| 6 | 100 | 89.6 |
| 7 | 100 | 46.9 |
| Cimetidine (for reference) | 100 | 80.3 |
|  | 30 | 59.1 |
|  | 10 | 25.3 |

Remark: Cimetidine (tradename of N-cyano-N'-methyl-N''-[2-[[(5-methyl-1H-imidazol-4-yl)methyl]thio]ethyl]- guanidine)

(3) Inhibitory actions on gastric lesion models

Two different types of gastric lesion models were induced in male Donryu rats (180 to 240 g) which had been deprived of food but allowed free access to water for 24 to 48 hours prior to experiments.

(a) Water-immersion stress-induced erosions:

Rats fasted for 24 hours before experiments were placed in a restraint cage. The animals were immersed vertically to the level of the xiphoid process in a water bath (21° C.) for 7 hours and then killed. The stomach of each rat was removed and inflated by injecting 10 ml of 1% formation to fix the inner and outer layers of the gastric walls. This formalin treatment was performed in all of the following experiments. Subsequently, the stomach was incised along a greater curvature and examined for any erosion in the glandular portion. Each test compound or a vehicle alone was given orally 10 minutes before stressing.

(b) HCl-ethanol-induced erosions

A hydrochloric acid-ethanol solution (150 mM HCl in 60% ethanol) was given orally to rats in a dose of 1 ml/200 g, which rats had been fasted for 24 hours before experiments. One hour later, each animal was killed and the stomach was examined for any erosion in the glandular portion. Each test compound or a vehicle alone was given orally 30 minutes before ethanol treatment.

The results are shown in Tables 3 and 4.

TABLE 3

| Test Compound No. | Dose (mg/kg) | Inhibition on Water-Immersion stress-induced erosions (%) |
| --- | --- | --- |
| 1 | 100 | 87 |
|  | 30 | 66 |
| Cimetidine (for reference) | 200 | 87 |
|  | 60 | 49 |

TABLE 4

| Test Compound No. | Dose (mg/kg) | Inhibition on HCl-Ethanol-induced Erosions (%) |
| --- | --- | --- |
| 1 | 30 | 97 |
|  | 10 | 37 |

The processes for the preparation of the sulfoxide derivatives of the invention are further described by the following examples.

EXAMPLE 1

Synthesis of 2-(2-Dimethylaminobenzylsulfinyl)imidazo[4,5-b]pyridine (Compound No. 1)

(1) Preparation of 2-mercaptoimidazo[4,5-b]pyridine

A mixture of 5 g of 2,3-diaminopyridine, 14.3 g of potassium xantogenate, 50 ml of ethanol and 10 ml of water was heated under reflux for 8 hrs., and then the solvents were removed from the reaction mixture under reduced pressure. The resulting solid residue was washed with acetone. The solid was then dissolved in water. The resulting aqueous solution was made acidic by addition of acetic acid to give a crystalline precipitate. The precipitate was collected by filtration and washed successively with water and ether to give 5 g of 2-mercaptoimidazo[4,5-b]pyridine, m.p.: higher than 250° C.

(2) Preparation of 2-(2-dimethylaminobenzylthio)imidazo[4,5-b]pyridine

To a solution of 1.71 g of sodium hydroxide in a mixture of 100 ml of ethanol and 5 ml of water was added 3.0 g of 2-mercaptoimidazo[4,5-b]pyridine. To thus obtained mixture was added 4.09 g of 2-dimethylaminobenzyl chloride hydrochloride, and thus obtained mixture was stirred at room temperature for 17.5 hrs. The solvent was then removed under reduced pressure, and the resulting residue was extracted with ethyl acetate.

The organic layer was washed successively with 5% aqueous sodium hydroxide solution, water and saturated aqueous sodium chloride solution, and then dried over sodium sulfate. The sodium sulfate was removed by filtration, and the solvent was removed to give a residue. The residue was warmed in ether, and the insolubles were removed by fitration.

The filtrate was concentrated to give 2.95 g of 2-(2-dimethylaminobenzylthio)imidazo[4,5-b]pyridine as a white powder.

$^1$H NMR (CDCl$_3$) δ: 2.96 (s, 6H), 4.44 (s, 2H), 7.02–8.2 (m, 7H).

(3) Preparation of 2-(2-dimethylaminobenzylsulfinyl)imidazo[4,5-b]pyridine (Compound No. 1)

In 50 ml of chloroform was dissolved 1.5 g of 2-(2-dimethylaminobenzylthio)imidazo[4,5-b]pyridine. To the resulting solution under chilling to −10° C. was added portionwise 1.36 g of m-chloroperbenzoic acid (purity: 80%). The reaction mixture was washed successively with saturated aqueous NaNCO$_3$ solution, water and saturated aqueous sodium chloride solution, and then dried over sodium sulfate. The sodium sulfate was removed by filtration, and the solvent was removed to give a solid residue. The residue was recrystallized from ethanol to give 1.15 g of 2-(2-dimethylaminobenzylsulfinylimidazo[4,5-b]pyridine as a white powder, m.p. 135°–136° C.

IR$\nu_{max}^{KBr}$ cm$^{-1}$: 1590, 1400, 1260, 1070, 1040, 940, 755.

$^1$H NMR (CDCl$_3$) δ: 2.60 (s, 6H), 4.48 and 4.84 (each d, 2H, J=14 Hz), 6.8–8.7 (m, 7H).

EXAMPLE 2

Synthesis of 2-(2-Pyridylmethylsulfinyl)quinoxaline (Compound No. 2)

(1) Preparation of 2-(2-pyridylmethylthio)quinoxaline

In 50 ml of acetone was dissolved 2.0 g of 2-mercaptoquinoxaline. To the solution were added 2.02 g of 2-picolyl chloride hydrochloride, 4.0 g of potassium carbonate and 5 ml of water. The resulting mixture was stirred at room temperature for 0.5 hr., and the solvent was removed under reduced pressure. The residue was extracted with chloroform after addition of chloroform and water. The organic layer was separated and dried over sodium sulfate. The sodium sulfate was removed by filtration, and the filtrate was placed under reduced pressure to remove the solvent. To the residue were added 20 ml of ethanol and 1.03 ml of conc. hydrchloric acid and then added ether. Thus precipitated crystals were washed with ethanol-ether (1:1) and dried under reduced pressure to give 2.09 g of 2-(2-pyridylmethylthio)quinoxaline hydrochloride as a yellow crystalline powder.

$^1$H NMR (CD$_3$OD) δ: 4.97 (s, 2H), 7.6–8.7 (m, 7H), 8.73 (s, 1H), 8.84 (m, 1H).

(2) Preparation of 2-(2-pyridylmethylsulfinyl)quinoxaline (Compound No. 2)

In a mixture of 20 ml of chloroform and 5 ml of methanol was dissolved 2.51 g of 2-(2-pyridylmethylthio)quinoxaline hydrochloride. To the chilled solution kept at a temperature of lower than 0° C. (temperature of solution) was portionwise added 1.95 g of m-chloroperbenzoic acid (purity: 70%). After the reaction was complete, chloroform and saturated aqueous NaHCO$_3$ solution were added to the reaction mixture. The organic layer was separated and dried over sodium sulfate. The sodium sulfate was then removed by filtration, and the solvent was evaporated under reduced pressure from the filtrate. The residue was purified by silica gel column chromatography (acetone/hexane), and recrystallized from ethanol/ether to give 0.27 g of 2-(2-pyridylmethyllsulfinyl)quinoxaline as a pale brown crystalline powder, m.p. 117°–122° C. (decompn.).

IR$\nu_{max}^{KBr}$ cm$^{-1}$: 1590, 1470, 1430, 1360, 1200, 1200, 1080, 1050, 995, 960, 765, 745.

$^1$H NMR (CDCl$_3$) δ: 4.43 and 4.70 (each d, 2H, J=14 Hz), 7.0–8.2 (m, 7H), 8.38 (m, 1H), 9.06 (s, 1H).

EXAMPLE 3

Synthesis of 3-Methyl-2-(2-pyridylmethylsulfinyl)quinoxaline (Compound No. 3)

(1) Preparation of 3-methyl-2-(2-pyridylmethylthio)quinoxaline

In a mixture of 70 ml of acetone and 7 ml of water were suspended 1.9 g of 2-mercapto-3-methylquinoxaline and 1.95 g of 2-picolyl chloride hydrochloride. To the suspension was added 4.0 g of potassium carbonate. The resulting mixture was stirred at room temperature for 1 hr., and the solvent was removed under reduced pressure. The residue was extracted with chloroform after addition of chloroform and water. The organic layer was separated and dried over sodium sulfate. The sodium sulfate was removed by filtration, and the filtrate was placed under reduced pressure to remove the solvent. The residue was dissolved in 20 ml of ethanol. To the solution under chilling with ice were successively added 3.2 ml of 5.2N ethanolic hydrochloric acid and ether to precipitate crystals. The crystals were collected by filtration to give 2.25 g of 3-methyl-2-(2-pyridylmethylthio)quinoxaline hydrochloride as a violet crystalline powder.

$^1$H NMR (CD$_3$OD) δ: 2.68 (s, 3H), 4.98 (s, 2H) 7.5–8.7 (m, 7H), 8.84 (m, 1H).

(2) Preparation of 3-methyl-2-(2-pyridylmethylsulfinyl)quinoxaline (Compound No. 3)

In a mixture of 36 ml of chloroform and 18 ml of methanol was dissolved 2.6 g of 3-methyl-2-(2-pyridylmethylthio)quinoxaline hydrochloride. To the chilled solution kept at a temperature of lower than 0° C. (temperature of solution) was added 1.77 g of m-chloroperbenzoic acid (purity 70%). After the reaction was complete, chloroform and saturated aqueous NaHCO$_3$ solution were added to the reaction mixture under chilling. The organic layer was separated and dried over sodium sulfate. The sodium sulfate was then removed by filtration, and the solvent was evaporated under reduced pressure from the filtrate. The residue was purified by silica gel column chromatography (chloroform/methanol), and recrystallized from ethyl/hexane to give 1.63 g of 3-methyl-2-(2-pyridylmethylsulfinyl)quinoxaline as an orange crystalline powder, m.p. 85°–88° C. (decompn.).

IR$\nu_{max}^{KBr}$ cm$^{-1}$: 1595, 1470, 1435, 1095, 1080, 1035, 770.

$^1$H NMR (CDCl$_3$) δ: 2.73 (s, 3H), 4.55 and 4.71 (each d, 2H, J=13 Hz), 7.0–8.3 (m, 7H), 8.39 (m, 1H).

EXAMPLE 4

Synthesis of 2-Methyl-3-(2-pyridylmethylsulfinyl)pyrido[2,3-b]pyrazine (Compound No. 4)

(1) Preparation of 2-methyl-3-(2-pyridylmethylthio)pyrido[2,3-b]pyrazine

To 1.67 g of 3-mercapto-2-methylpyrido[2,3-b]pyrazine were added 10 ml of ethanol and a solution of 1.15 g of 2-picolyl chloride hydrochloride and 0.67 g of sodium hydroxide. The obtained mixture was heated under refluxing for 1.5 hrs, and then the solvent was removed under reduced pressure. The residue was extracted with ethyl acetate. The extract was washed with water and saturated aqueous sodium chloride solution, and dried over sodium sulfate. The sodium sulfate was removed by filtration. and the filtrate was placed under reduced pressure to remove the solvent. The residue was dissolved in 20 ml of acetonitrile, and the insolubles were removed by filtration. The filtrate was concentrated to give 1.5 g of 2-methyl-3-(2-pyridylmethylthio)pyrido[2,3-b]pyrazine as a brown oil.

$^1$H NMR (CDCl$_3$) δ: 2.74 (s, 3H), 4.72 (s, 2H), 7.0–9.0 (m, 7H).

(2) Preparation of 2-methyl-3-(2-pyridylmethylsulfinyl)pyrido[2,3-b]pyrazine (Compound No. 4)

In 14 ml of chloroform was dissolved 1.4 g of 2-methyl-3-(2-pyridylmethylthio)pyrido[2,3-b]pyrazine. To the solution under chilling with ice was added portionwise 1.1 g of m-chloroperbenzoic acid (purity: 80%). The reaction mixture was then left to have room temperature, and poured into saturated aqueous NaHCO$_3$ solution. The aqueous mixture was extracted with chloroform. The chloroform layer was washed with water and saturated aqueous sodium chloride solution, and dried over sodium sulfate. The sodium sulfate was then removed by filtration, and the solvent was evaporated under reduced pressure from the filtrate. The residue was purified by silica gel column chromatography (chloroform/methanol), to give 420 mg of 2-methyl-3-(2-pyridylmethylsulfinyl)pyrido[2,3-b]pyrazine as a brown crystalline powder, m.p. 120°–125° C. (decompn.).

IRυ$_{max}^{KBr}$ cm$^{-1}$: 3460, 1580, 1440, 1270, 1080, 1069, 795.

$^1$H NMR (CDCl$_3$) δ: 2.78 (s, 3H), 4.57 and 4.74 (each d, 2H, J=13 Hz), 7.0–7.9 (m, 4H), 8.20–8.38 (m, 1H), 8.50 (dd, 1H, J=2 Hz, 8 Hz), 9.16 (dd, 1H, J=2 Hz, 4 Hz).

EXAMPLE 5

. Synthesis of 2-(2-Dimethylaminobenzylsulfinyl)quinoxaline (Compound No. 5)

(1) Preparation of 2-(2-dimethylaminobenzylthio)quinoxaline

To a solution of 1 g of 2-mercaptoquinoxaline in 40 ml of ethanol was added a solution of 530 mg of sodium hydroxide in 2 ml of water, and subsequently added 1.27 g of 2-dimethylaminobenzyl chloride hydrochloride. The resulting mixture was stirred at room temperature for 18 hrs., and the solvent was removed under reduced pressure. The residue was extracted with ethyl acetate. The organic layer was washed successively with 5% aqueous sodium hydroxide solution, water, and saturated aqueous sodium chloride solution, and dried over soidum sulfate. The sodium sulfate was removed by filtration, and the filtrate was placed under reduced pressure to remove the solvent. The residue was purified by silica gel column chromatography (hexane/acetone) to give 1.5 g of 2-(2-dimethylaminobenzylthio)quinoxaline as a yellow oil.

$^1$H NMR (CDCl$_3$) δ: 2.76 (s, 6H), 4.72 (s, 2H), 6.8–7.6 (m, 9H).

(2) Preparation of 2-(2-dimethylaminobenzylsulfinyl)quinoxaline (Compound No. 5)

In 50 ml of chloroform was dissolved 1.47 g of 2-(2-dimethylaminobenzylthio)quinoxaline. To the chilled solution kept at −10° C. was portionwise added 1.54 g of m-chloroperbenzoic acid (purity: 80%). To the reaction liquid were washed successively with saturated aqueous NaHCO$_3$ solution, water and saturated aqueous sodium chloride solution, and dried over sodium sulfate. The sodium sulfate was then removed by filtration, and the solvent was evaporated under reduced pressure from the filtrate. The residue was purified by silica gel column chromatography (hexane/acetone) to give 330 mg of 2-(2-dimethylaminobenzylsulfinyl)quinoxaline as a yellow powder, m.p. 114°–115° C.

IRυ$_{max}^{KBr}$ cm$^{-1}$: 1485, 1445, 1080, 1045, 945, 760.

$^1$H NMR (CDCl$_3$) δ: 2.40 (s, 6H), 4.46 and 4.66 (each d, 2H, J=14 Hz), 6.9–8.2 (m, 9H).

EXAMPLE 6

Synthesis of 2-(2-Dimethylaminobenzylsulfinyl)-3-methylquinoxaline (Compound No. 6)

(1) Preparation of 2-(2-dimethylaminobenzylthio)-3-methylquinoxaline

In a mixture of 50 ml of acetone and 5 ml of water were suspended 2.80 g of 2-mercapto-3-methylquinoxaline, 3.28 g of 2-dimethylaminobenzyl chloride hydrochloride, and 8.0 g of potassium carbonate. The resulting mixture was stirred at room temperature for 40 min., and the solvent was removed under reduced pressure. The residue was extracted with chloroform after addition of chloroform and water. The organic layer was separated and dried over sodium sulfate. The sodium sulfate was removed by filtration, and the filtrate was placed under reduced pressure to remove the solvent. The residue was diluted with 50 ml of ethanol. To the solution under chilling with ice were successively added 1.33 ml of conc. hydrochloric acid and ether to precipitate crystals. The crystals were collected by filtration to give 4.56 of 2-(2-dimethylaminobenzylthio)-3-methylquinoxaline hydrochloride as a dark brown crystalline powder.

$^1$H NMR (Cd$_3$OD/CDCl$_3$) δ: 2.67 (s, 3H), 3.46 (s, 6H), 5.00 (s, 2H), 7.4–8.1 (m, 8H).

(2 Preparation of 2-(2-dimethylaminobenzylsulfinyl)-3-methylquinoxaline (Compound No. 6)

In a mixture of 10 ml of chloroform and 10 ml of methanol was dissolved 1.73 g of 2-(2-dimethylaminobenzylthio)-3-methylquinoxaline hydrochloride. To the chilled solution kept at a temperature of lower than 0° C. (temperature of solution) was portionwise added 1.14 g of m-chloroperbenzoic acid (purity:

80%). After the reaction was complete, chloroform and saturated aqueous NaHCO$_3$ solution were added to the reaction mixture. The organic layer was separated and dried over sodium sulfate. The sodium sulfate was then removed by filtration, and the solvent was evaporated under reduced pressure from the filtrate. The residue was purified by silica gel column chromatography (chloroform/methanol), and recrystallized from ethyl acetate/hexane to give 0.51 g of 2-(2-dimethylaminobenzylsulfinyl)-3-methylquinoxaline as a pale brown crystalline powder, m.p. 68°–70° C. (decompn.).

IR$\nu_{max}^{KBr}$ cm$^{-1}$: 1590, 1160, 1090, 1080, 1070, 1045, 945, 760.

$^1$H NMR (CDCl$_3$) δ: 2.42 (s, 6H), 2.49 (s, 3H), 4.44 and 4.73 (each d, 2H, J=12 Hz), 6.8–8.3 (m, 8H).

EXAMPLE 7

Synthesis of 2-(2-Dimethylaminobenzylsulfinyl)-3,6,7-trimethylquinoxaline (Compound No. 7)

(1) Preparation of 2-(2-dimethylaminobenzylthio)-3,6,7-trimethylquinoxaline

To a mixture of 50 ml of acetone and 5 ml of water were added 4.08 g of 2-mercapto-3,6,7-trimethylquinoxaline, 4.12 g of 2-dimethylaminobenzyl chloride hydrochloride, and 10.0 g of potassium carbonate. The resulting mixture was stirred at room temperature for 2 hrs., and the solvent was removed under reduced pressure. To the residue were added water and chloroform. After the insolubles were removed by filtration, the organic layer was separated and dried over sodium sulfate. The sodium sulfate was removed by filtration, and the filtrate was placed under reduced pressure to remove the solvent. To the residue was added hexane, and the insolubles were removed by filtration. The filtrate was dried under reduced pressure to give 6.48 g of 2-(2-dimethylaminobenzylthio)-2,6,7-trimethylquinoxaline hydrochloride as a pale orange crystalline powder.

$^1$H NMR (CDCl$_3$) δ: 2.43 (s, 6H), 2.61 (s, 3H), 2.75 (s, 6H), 4.73 (s, 2H), 6.8–7.8 (m, 6H).

(2) Preparation of 2-(2-dimethylaminobenzylsulfinyl)-3,6,7-trimethylquinoxaline (Compound No. 7)

In a mixture of 35 ml of chloroform and 3 ml of methanol was dissolved 3.71 g of 2-(2-dimethylaminobenzylthio)-3,6,7-trimethylquinoxaline. To the chilled solution kept at a temperature of lower than 0° C. (temperature of solution) was slowly added 2.45 g of m-chloroperbenzoic acid (purity: 80%). After the reaction was complete, chloroform and saturated aqueous NaHCO$_3$ solution were added to the reaction mixture. The organic layer was separated and dried over sodium sulfate. The sodium sulfate was then removed by filtration, and the solvent was evaporated under reduced pressure from the filtrate. The residue was purified by silica gel column chromatography (acetone/hexane). The eluate was concentrated and the resulting residue was crystallized from ether/hexane to give 1.12 g of 2-(2-dimethylaminobenzylsulfinyl)-3,6,7-trimethylquinoxaline as a yellow crystalline powder, m.p. 83°–88° C. (decompn.).

IR$\nu_{max}^{KBr}$ cm$^{-1}$: 2930, 1490, 1480, 1445, 1090, 1070, 1050, 870, 760.

$^1$H NMR (CDCl$_3$) δ: 2.46 (s, 9H), 2.51 (s, 6H), 4.44 and 4.71 (each d, 2H, J=12 Hz), 6.8–7.4 (m, 4H), 7.76 and 8.00 (each s, 2H).

EXAMPLE 8

Synthesis of 2-(2-Diethylaminobenzylsulfinyl)-3-methylquinoxaline (1) Preparation of 2-(2-diethylaminobenzylthio)-3-methylquinoxaline To a solution of 0.73 g of sodium hydroxide in a mixture of 2 ml of water and 50 ml of ethanol were added successively 1.5 g of 2-mercapto-3-methylquinoxaline and 1.99 g of 2-diethylaminobenzyl chloride hydrochloride. The resulting mixture was stirred at room temperature for 3 hrs., and the solvent was removed under reduced pressure. The residue was extracted with ethyl acetate. The organic layer was washed successively with 5% aqueous sodium hydroxide solution, water and saturated aqueous sodium chloride solution, and then dried over sodium sulfate. The sodium sulfate was removed by filtration, and the filtrate was placed under reduced pressure to removed the solvent. The residual oil was purified by silica gel column chromatography (hexane/acetone) to give 1.74 g of 2-(2-diethylaminobenzylthio)-3-methylquinoxaline as a yellow oil.

$^1$H NMR (CDCl$_3$) δ: 1.04 (t, 6H, J=8 Hz), 2.64 (s, 3H), 3.04 (q, 4H, J=8 Hz), 4.76 (s, 2H), 6.8–8.0 (m, 8H).

(2) Preparation of 2-(2-diethylaminobenzylsulfinyl)-3-methylquinoxaline

In 50 ml of chloroform was dissolved 1.7 g of 2-(2-diethylaminobenzylthio)-3-methylquinoxaline. To the chilled solution kept at −10° C. was portionwise added 1.21 g of m-chloroperbenzoic acid (purity: 80%). The reaction liquid was then washed successively with saturated aqueous NaHCO$_3$ solution, water and saturated aqueous sodium chloride solution, and dried over sodium sulfate. The sodium sulfate was then removed by filtration, and the solvent was evaporated under reduced pressure from the filtrate. The residual oil was purified by silica gel column chromatography (hexane/acetone) to give 1.2 g of 2-(2-diethylaminobenzylsulfinyl)-3-methylquinoxaline as a yellow oil.

$^1$H NMR (CDCl$_3$) δ: 0.96 (t, 6H, J=8 Hz), 2.52 (s, 3H), 2.92 (q, 4H, J=8 Hz), 4.44 and 4.70 (each d, 2H, J=12 Hz), 6.8–8.4 (m, 8H).

EXAMPLE 9

Synthesis of 2-[2-(Isobutylamino)benzylsulfinyl]imidazo[4,5-b]pyridine (1) Preparation of 2-(isobutylamino)benzyl chloride (HCl salt)

To a dispersion of 13.0 g of lithium aluminum hydride in 500 ml of diethyl ether was dropwise added under chilling with ice a solution of 27.0 g of methyl 2-(isobutylylamino)benzoate in 75 ml of diethyl ether over a period of 30 min. The resulting mixture was stirred for one hour at room temperature and further stirred under reflux for one hour. The mixture was then chilled by ice, and remaining lithium aluminum hydride was decomposed by addition of saturated sodium sulfate solution. The etheral phase was separated, and placed under reduced pressure to distill off the ether.

There was obtained 21.2 g (yield: 97%) of 2-(isobutylamino)benzyl alcohol as a yellow oil.

In 190 ml of conc. hydrochloric acid was dissolved 19.1 g of 2-(isobutylamino)benzyl alcohol, and the solution was heated in a sealed tube at 100° C. for 40 min. The reaction mixture was stirred for 30 min. under chilling with ice and the precipitated crystals were collected by filtration. The collected crystals were washed successively with hydrochloric acid and acetone and dried to give 16.9 g (yield: 68%) of 2-isobutylamino)benzyl chloride hydrochloride as a white crystalline product.

$^1$H NMR (CD$_3$OD) δ: 1.12 (d, 6H, J=7 Hz), 2.18 (m, 1H), 3.27 (d, 2H, J=7 Hz), 4.79 (s, 2H), 7.3–7.7 (m, 4H).

(2) Preparation of 2-[2-(isobutylamino)benzylthio]imidazo[4,5-b]pyridine

To a dispersion of 0.96 of 2-mercaptoimidazo[4,5-b]pyridine in 30 ml of ethanol was added at once 1.5 g of 2-(isobutylamino)benzyl chloride hydrochloride at room temperature under stirring. The resulting mixture was further stirred for one hour. To the mixture was added 30 ml of diethyl ether, and the precipitated crystals were collected by filtration and washed with a mixture of ethanol and diethyl ether (1/1 in volume). The obtained powdery product was added portionwise to a mixture of 30 ml o fchloroform and 30 ml of a saturated NaHCO$_3$ solution for neutralization. The organic phase was separated, washed with a saturated aqueous sodium chloride solution, and dried over sodium sulfate. The solvent was then distilled off under reduced pressure and the residue was crystallized by addition of diethyl ether and hexane. The crystalline product was collected by filtration, washed with a mixture of diethyl ether and hexane (1/1 in volume) and dried to give 985 mg (yield: 49.3%) of 2-[2-(isobutylamino)benzylthio]imidazo[4,5-b]pyridine as a white crystalline powder.

$^1$H NMR (CDCl$_3$) δ: 0.90 (d, 6H, J=8 Hz), 1.50–2.00 (m, 1H), 2.92 (d, 2H, J=7 Hz), 4.68 (s, 2H) 6.4–7.4 (m, 5H), 7.86 (d, 1H, J=8 Hz), 8.18 (d, 1H, J=6 Hz).

(3) Preparation of 2-[2-(isobutylamino)benzylsulfinyl]imidazo[4,5b]pyridine

In 20 ml of chloroform was dissolved 900 mg of 2-[2-(isobutylamino)benzylthio]imidazo[4,5-b]pyridine. To the resulting solution was portionwise added under chilling with ice 618 mg of m-chloroperbenzoic acid (purity: 80%) over a period of 30 min. To the mixture was added a saturated NaHCO$_3$ solution, and the resulting mixture was then stirred. The organic phase was separated and extracted successively with 20 ml of 0.1N NaOH and 10 ml of 0.1N NaOH. The alkaline extracts were combined and neutralized by NH$_4$Cl, and the deposited oil was extracted with chloroform. The chloroform extract was washed with a saturated aqueous sodium chloride solution, dried over sodium sulfate and placed under reduced pressure to distill off the solvent. The residue was crystallized by addition of diethyl ether. The crystalline product was washed with diethyl ether to give 195 mg of 2-[2-(isobutylamino)benzylsulfinyl]imidazo[4,5-b]pyridine as a pale yellow crystalline powder. m.p.: 116° C. (decompn.).

IRυ$_{max}^{KBr}$ cm$^{-1}$: 2950, 1600, 1585, 1465, 1400, 1310, 1260, 1020, 765, 740.

$^1$H NMR (CDCl$_3$) δ: 0.99 (d, 6H, J=7 Hz), 1.6–2.1 (m, 1H), 2.78 (d, 2H, J=7 Hz), 4.38 and 4.69 (each d, 2H, J=14 Hz) 6.3–7.1 (m, 4H), 8.14 (d, 1H, J=8 Hz), 8.62 (d, 1H, J=5 Hz).

EXAMPLE 10

Synthesis of 2-[2-(Methylamino)benzylsulfinyl]imidazo[4,5-b]pyridine (1) Preparation of 2-(methylamino)benzyl chloride (HCl salt)

Methyl 2-(methylamino)benzoate was treated in the same manner as in Example 9-(1) to give 2-(methylamino)benzyl chloride hydrochloride as a white crystalline product.

(2) Preparation of 2-[2-(methylamino)benzylthio]imidazo[4,5-b]pyridine

To a dispersion of 1.51 g of 2-mercaptoimidazo[4,5-b]pyridine in 25 ml of ethanol was added at once 1.92 g of 2-(methylamino)benzyl chloride hydrochloride at room temperature under stirring. The resulting mixture was further stirred for 3.5 hours. The precipitated crystals were collected by filtration and washed with ethanol. The obtained crystals were added portionwise to a mixture of 100 ml of chloroform and 100 ml of 1N NaOH solution for neutralization. The aqueous NaOH phase was separated, and to this phase were successively added 200 ml of chloroform and a saturated ammonium chloride solution until the aqueous phase showed no turbidity upon addition of the solution. The chloroform phase was separated, washed with a saturated aqueous sodium chloride solution, and dried over sodium sulfate. The solvent was then distilled off under reduced pressure and the residue was crystallized by addition of diethyl ether. The crystalline product was collected by filtration and dried to give 1.84 g (yield: 68.1%) of 2-[2-(methylamino)benzylthio]imidazo[4,5-b]pyridine as a white crystalline powder.

$^1$H NMR (CDCl$_3$) δ: 2.85 (s, 3H), 4.57 (s, 2H), 6.5–7.4 (m, 5H), 7.6–8.3 (m, 2H).

(3) Preparation of 2-[2-(methylamino)benzylsulfinyl]imidazo[4,5-b]pyridine

In a mixture of 1 ml of methanol and 30 ml of chloroform was dissolved 1.5 g of 2-[2-(methylamino)benzylthio]imidazo[4,5-b]pyridine. To the resulting solution was portionwise added under chilling with ice and aqueous sodium chloride solution to −5° C. 1.08 g of m-chloroperbenzoic acid (purity: 80%) over a period of 20 min., maintaining the temperature of the solution at −5° C.±3° C. The reaction mixture was stirred for additional 15 min. at the same temperature, and to the mixture was added a saturated NaHCO$_3$ solution. The resulting mixture was then stirred. The organic phase was separated and extracted with two poritons of 14 ml of 0.1N NaOH. The alkaline extracts were combined and neutralized by NH$_4$Cl, and the deposited oil was extracted with chloroform. The chloroform extract was washed with a saturated aqueous sodium chloride solution, dried over sodium sulfate and placed under reduced pressure to distill of the solvent. The residue was crystallized by addition of acetonitrile to give 2-[2-(methylamino)benzylsulfinyl]imidazo[4,5-b]pyridine. m.p.: 120° C. (decompn.).

IVυ$_{max}^{KBr}$ cm$^{-1}$: 3370, 1600, 1585, 1520, 1425, 1400, 1305, 1270, 1050, 740.

$^1$H NMR (CDCl$_3$) δ: 2.63 (s, 3H), 4.36 and 4.65 (each d, 2H, J=14 Hz), 6.3–7.6 (m, 5H), 8.14 (d, 1H, J=8 Hz), 8.58 (d, 1H, J=4 Hz).

EXAMPLE 11

Synthesis of 2-[2-(N-Isobutyl-N-methylamino)benzylsulfinyl]imidazo[4,5-b]pyridine 2-Mercaptoimidazo[4,5-b]pyridine and 2-(N-isobutyl-N-methylamino)benzyl chloride hydrochloride were reacted in an aqueous ethanol solution in the presence of sodium hydroxide to obtain 2-[2-(N-isobutyl-N-methylamino)benzylthio]imidazo[4,5-b]pyridine in the same manner as in Example 1-(2). The obtained 2-[2-(N-isobutyl-N-methylamino)benzylthio]imidazo[4,5-b]pyridine was oxidized by m-chloroperbenzoic acid in chloroform in the same manner as in Example 9-(3) to give 2-[2-(N-isobutyl-N-methylamino)benzylsulfinyl]imidazo[4,5-b]pyridine as a pale yellow crystalline product. m.p.: 116°–118° C. (decompn.)

IR$\nu_{max}^{KBr}$ cm$^{-1}$: 2940, 1585, 1485, 1425, 1400, 1265, 1050, 760.

$^1$H NMR (CDCl$_3$) δ: 0.91 (d, 6H, J=7 Hz), 2.59 (s, 3H), 2.64 (d, 2H), 4.52 and 4.94 (each d, 2H, J=13 Hz), 6.8–7.5 (m, 5H), 8.17 (d, 1H, J=8 Hz), 8.73 (d, 1H, J=5 Hz).

EXAMPLE 12

Synthesis of 2-[2-(N-Cyclopentylamino)benzylsulfinyl]imidazo[4,5-b]pyridine

2-Mercaptoimidazo[4,5-b]pyridine and 2-(N-cylopentylamino)benzyl chloride hydrochloride were reacted in an aqueous ethanol solution to obtain 2-[2-(N-cyclopentylamino)benzylthio[-imidazo[4,5-b]pyridine in the same manner as in Example 9-(2). The obtained 2-[2-(N-cyclopentylamino)benzylthio]imidazo[4,5-b]pyridine was oxidized by m-chloroperbenzoic acid in chloroform in the same manner in Example 9-(3) to give 2-[2-(N-cyclopentylamino)benzylsulfinyl]imidazo[4,5-b]pyridine as a pale yellow crystalline product. m.p.: 134° C. (decompn.)

IR$\nu_{max}^{KBr}$ cm$^{-1}$: 2950, 1600, 1590, 1505, 1425, 1400, 1305, 1265, 1050, 745.

$^1$H NMR (CDCl$_3$) δ: 1.0–2.2 (m, 8H), 3.4–3.9 (m, 1H), 4.34 and 4.62 (each d, 2H, J=6 Hz), 6.3–7.5 (m, 5H), 8.08 (d, 1H, J=8 Hz), 8.58 (d, 1H, J=5 Hz).

Examples of the preparations using the sulfoxide derivative of the invention are described by the following examples.

EXAMPLE 13

Preparation in the form of pellet

A pellet (220 mg) containing:

| | |
|---|---|
| active component | 50 mg |
| lactose | 103 mg |
| starch | 50 mg |
| magnesium stearate | 2 mg |
| hydroxypropylcellulose | 15 mg | was obtained

EXAMPLE 14

Preparation in the form of capsule

A gelatin-shell hard capsule containing 350 mg of the core portion consisting of:

| | |
|---|---|
| active component | 40 mg |
| lactose | 200 mg |
| starch | 70 mg |
| polyvinylpyrrolidone | 5 mg |
| crystalline cellulose | 35 mg | was obtained.

EXAMPLE 15

Preparation in the form of granules One gram of granules containing:

| | |
|---|---|
| active component | 200 mg |
| lactose | 450 mg |
| corn starch | 300 mg |
| hydroxypropylcellulose | 50 mg | was obtained.

We claim:

1. A sulfoxide derivative having the formula (I):

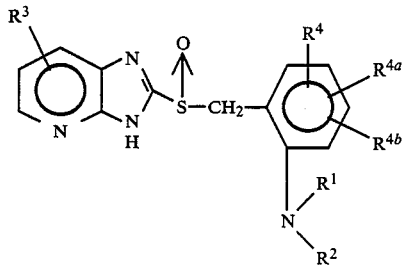

wherein each of R$^1$ and R$^2$ independently is hydrogen, an alkyl group having 1 to 6 carbon atoms which may be substituted with hydroxyl, phenyl, a phenylalkyl group containing an alkyl chain of 1 to 4 carbon atoms, and a cycloalkyl group having 5 to 8 carbon atoms, R$^1$ and R$^2$ may form together with the adjacent nitrogen atom a heterocyclic group having 4 to 6 carbon atoms, and each of R$^3$, R$^4$, R$^{4a}$ and R$^{4b}$ independently is hydrogen, halogen, hydroxyl, an alkoxy group having 1 to 6 carbon atoms which may be substituted with fluorine, an alkyl group having 1 to 6 carbon atoms, or trifluoromethyl.

2. The sulfoxide derivative as claimed in claim 1, wherein each of R$^3$, R$^4$, R$^{4a}$ and R$^{4b}$ is hydrogen.

3. The sulfoxide derivative as claimed in claim 1, wherein each of R$^1$ and R$^2$ independently is hydrogen, an alkyl group having 1 to 6 carbon atoms or a cycloalkyl group having 5 to 8 carbon atoms.

4. The sulfoxide derivative as claimed in claim 1, wherein each of R$^1$ and R$^2$ independently is methyl, ethyl, propyl, isobutyl, cyclopentyl or cyclohexyl.

5. The sulfoxide derivative as claimed in claim 1, wherein said derivative is:

2-(2-dimethylaminobenzylsulfinyl)imidazo[4,5-b]pyridine;

2-(2-dimethylaminobenzylsulfinyl)-7-methoxyimidazo[4,5-b]pyridine;

2-(2-dimethylaminobenzylsulfinyl)-7-methylimidazo[4,5-b]pyridine;
2-(2-diethylaminobenzylsulfinyl)imidazo[4,5-b]pyridine;
2-(2-dimethylamino-5-methylbenzylsulfinyl)imidazo[4,5-b]pyridine;
2-(2-dimethylamino-4-chlorobenzylsulfinyl)imidazo[4,5-b]pyridine;
2-(2-dimethylamino-5-methoxybenzylsulfinyl)imidazo[4,5-b]pyridine;
2-(2-dimethylamino-6-methylbenzylsulfinyl)imidazo[4,5-b]pyridine;
2-(2-dimethylamino-4-fluorobenzylsulfinyl)imidazo[4,5-b]pyridine;
2-(2-dimethylaminobenzylsulfinyl)-6-methylimidazo[4,5-b]pyridine;
2-(2-methylaminobenzylsulfinyl)imidazo[4,5-b]pyridine;
2-(2-isobutylaminobenzylsulfinyl)imidazo[4,5-b]pyridine;
2-(2-cyclopentylaminobenzylsulfinyl)imidazo[4,5-b]pyridine;
2-(2-cyclohexylaminobenzylsulfinyl)imidazo[4,5-b]pyridine;
2-[2-(N-isobutyl-N-methylamino)benzylsulfinyl]imidazo[4,5-b]pyridine;
2-[2-(N-ethyl-N-methylamino)benzylsulfinyl]imidazo[4,5-b]pyridine;
2-(2-methylamino-5-methylbenzylsulfinyl)imidazo[4,5-b]pyridine;
2-(2-isobutylamino-5-methylbenzylsulfinyl)imidazo[4,5-b]pyridine;
2-(5-methoxy-2-methylaminobenzylsulfinyl)imidazo[4,5-b]pyridine;
2-(2-cyclopentylamino-5-methylaminobenzylsulfinyl)imidazo[4,5-b]pyridine;
2-(2-aminobenzylsulfinyl)imidazo[4,5-b]pyridine;
2-(2-piperidinobenzylsulfinyl)imidazo[4,5-b]pyridine;
2-(2-methylamino-5-hydroxybenzylsulfinyl)imidazo[4,5-b]pyridine;
2-(2-dimethylamino-5-hydroxybenzylsulfinyl)imidazo[4,5-b]pyridine; or
2-(2-hydroxyethylaminobenzylsulfinyl)imidazo[4,5-b]pyridine.

* * * * *